United States Patent
Herrmann et al.

(10) Patent No.: US 10,370,392 B2
(45) Date of Patent: Aug. 6, 2019

(54) DOPED HYDRIDOSILANE COMPOSITIONS, AND METHOD FOR PRODUCING SAME

(71) Applicant: Evonik Degussa GmbH, Essen (DE)

(72) Inventors: Stephan Herrmann, Loerrach Brombach (DE); Odo Wunnicke, Muenster (DE); Matthias Patz, Bottrop (DE); Miriam Deborah Malsch, Essen (DE); Harald Stueger, Graz (AT)

(73) Assignee: Evonik Degussa GmbH, Essen (DE)

( * ) Notice: Subject to any disclaimer, the term of this patent is extended or adjusted under 35 U.S.C. 154(b) by 0 days.

(21) Appl. No.: 16/062,195

(22) PCT Filed: Dec. 6, 2016

(86) PCT No.: PCT/EP2016/079885
§ 371 (c)(1),
(2) Date: Jun. 14, 2018

(87) PCT Pub. No.: WO2017/102434
PCT Pub. Date: Jun. 22, 2017

(65) Prior Publication Data
US 2019/0023723 A1     Jan. 24, 2019

(30) Foreign Application Priority Data

Dec. 15, 2015 (DE) .................. 10 2015 225 289

(51) Int. Cl.
| | | |
|---|---|---|
| *C07F 5/02* | (2006.01) | |
| *C01B 33/04* | (2006.01) | |
| *H01L 31/068* | (2012.01) | |
| *C08L 83/16* | (2006.01) | |
| *C08G 77/60* | (2006.01) | |

(52) U.S. Cl.
CPC .............. *C07F 5/025* (2013.01); *C01B 33/04* (2013.01); *C08L 83/16* (2013.01); *H01L 31/068* (2013.01); *C08G 77/60* (2013.01)

(58) Field of Classification Search
CPC ......... C01B 33/04; C07F 5/025; C08G 77/60; C08L 83/16; H01L 31/068
See application file for complete search history.

(56) References Cited

U.S. PATENT DOCUMENTS

| | | | | |
|---|---|---|---|---|
| 6,132,492 | A * | 10/2000 | Hultquist | B01D 53/0446 95/45 |
| 2012/0042951 | A1 | 2/2012 | Stuetzel et al. | |
| 2014/0142242 | A1 | 5/2014 | Gerbec | |
| 2015/0329680 | A1 * | 11/2015 | Traut | C07F 7/0827 528/31 |
| 2016/0145439 | A1 | 5/2016 | Woebkenberg et al. | |
| 2016/0297997 | A1 | 10/2016 | Cadiz Bedini | |

FOREIGN PATENT DOCUMENTS

| | | |
|---|---|---|
| DE | 10 2010 002 405 A1 | 9/2011 |
| DE | 102012221669 A1 | 5/2014 |
| DE | 102013010102 A1 | 12/2014 |
| DE | 102013020518 A1 | 6/2015 |
| WO | WO 2009/111191 A1 | 9/2009 |
| WO | WO 2010/125081 A2 | 11/2010 |

OTHER PUBLICATIONS

International Search Report dated Feb. 10, 2017, in PCT/EP2016/079885, filed Dec. 6, 2016.
Office Action dated Aug. 24, 2016 in German Patent Application No. 10 2015 225 289.2 (with English language translation of categories of cited documents).

* cited by examiner

*Primary Examiner* — Yevgeny Valenrod
*Assistant Examiner* — Blaine G Doletski
(74) *Attorney, Agent, or Firm* — Oblon, McClelland, Maier & Neustadt, L.L.P.

(57) ABSTRACT

The present invention relates to compositions comprising at least one hydridosilane of the generic formula $Si_nH_m$ with $n \geq 5$ and $m=(2n)$ and $(2n+2)$ and at least one compound of the formula $H_nB(OR)_{3-n}$ with $R=C_1\text{-}C_{10}$-alkyl, $C_6\text{-}C_{10}$-aryl, $C_7\text{-}C_{14}$-aralkyl, halogen, $n=0, 1, 2$, to processes for preparation thereof and use thereof.

9 Claims, No Drawings

DOPED HYDRIDOSILANE COMPOSITIONS, AND METHOD FOR PRODUCING SAME

The present invention relates to doped compositions, to processes for production thereof, and to the use thereof.

For the semiconductor industry in particular, the production of silicon-containing layers is of interest. Silicon-containing layers can be deposited from the gas phase in vacuum chambers, for example via PECVD. Gas phase processes, however, are technically complex and often do not lead to layers of the desired quality. For this reason, liquid phase processes are often preferred for production of silicon-containing layers.

For this reason, compositions with which silicon-containing layers can be produced via liquid phase processes are of great interest.

In this context, it is not only liquid phase processes for production of intrinsic, i.e. undoped, silicon-containing layers that are of interest. Particularly for the production of p- or n-doped silicon-containing layers, processes for production of doped silicon-containing layers and the compositions used therein are of interest.

For production of p-doped, especially boron-doped, silicon-containing layers, there are already various liquid phase processes and compositions usable for the purpose. For instance, U.S. Pat. No. 5,866,471 A discloses a process for producing p-doped silicon-containing layers, in which an undoped coating composition is applied to a substrate and converted to a doped silicon-containing layer in the presence of a p-dopant-containing atmosphere. However, a disadvantage of this process is that it is very complex especially in terms of apparatus.

U.S. Pat. No. 5,866,471 A additionally also discloses a pure liquid phase process for production of doped silicon-containing layers, in which a formulation comprising a dopant and a silicon-containing precursor is applied to a substrate and subsequently converted to a semiconductor layer. However, the dopants used are either alkylated/arylated compounds of the dopant (for example $BPh_3$, $BMePh_2$ or $B(t-Bu)_3$) or compounds having a bond between a silicon atom and a dopant atom (for example $B(SiMe_3)_3$, $PhB(SiMe_3)_2$ or $Cl_2B(SiMe_3)$). However, the former compounds lead to disadvantageous carbon-containing layers because of the alkyl/aryl radical of the compounds. The latter compounds mentioned are not commercially available and hence first have to be synthesized in a complex manner. Furthermore, they are disadvantageous for the reasons already mentioned if they are alkylated/arylated.

EP 1 715 509 B1 and EP 1 085 579 A1 also disclose a process for producing doped silicon-containing layers, in which a composition comprising a compound of the formula $Si_aX_bY_c$ where Y may be a boron atom is used. However, these compounds too first have to be synthesized in a complex manner.

EP 1 640 342 A1 and EP 1 357 154 A1 disclose silicon-forming compositions which may include a silane polymer and an organic solvent and optionally a material containing an element of the 3rd main group, one of which is boron. Illustrative compounds are those specified in JP 2000-031066 A, i.e. $B_2H_6$, $B_4H_{10}$, $B_5H_9$, $B_6H_{10}$, $B_{10}H_{14}$, $B(CH_3)_3$, $B(C_2H_5)_3$, and $B(C_6H_5)_3$. However, the corresponding alkylated or arylated boron compounds, as already stated, lead to disadvantageous carbon-containing layers. The use of the boranes mentioned is additionally disadvantageous because of their high toxicity.

US 2008/0022897 A1 also discloses, inter alia, silicon-forming compositions which may include a dopant source. The boron-containing dopants described may be boron-containing heterocyclosilane compounds or other compounds having boron-silicon bonds which have the disadvantage already described of first having to be synthesized in a complex manner. Likewise disclosed are hydrogen-containing alkylated, arylated or arylalkylated boron compounds which are disadvantageous either because of their toxicity, which has already been mentioned, or because of their propensity to lead to carbon-containing layers.

DE 10 2010 040 231 A1 additionally describes formulations which are suitable for production of p-doped silicon-containing layers and comprise a silicon compound and at least one compound from the group of hydroborating agents, which may be a complex of $BH_3$ with a complexing agent selected from the group consisting of THF, $NR_3$ and $SR'_2$. Because of the metastability of the compounds mentioned, however, controlled addition of the dopants is not assured.

The problem addressed by the present invention is thus that of avoiding the disadvantages of the prior art. More particularly, the problem addressed by the present invention is that of providing formulations comprising dopants, with which readily available and stable compounds of low toxicity can be used to efficiently produce carbon-free silicon-containing layers as well.

The problem which is thus addressed is surprisingly solved by the inventive compositions comprising at least one hydridosilane of the generic formula $Si_nH_m$ with n≥5 and m=(2n) to (2n+2) and at least one compound of the formula $H_nB(OR)_{3-n}$ with R=$C_1$-$C_{10}$-alkyl, $C_6$-$C_{10}$-aryl, $C_7$-$C_{14}$-arylalkyl, halogen, n=0, 1, 2, correspondingly referred to as derivatives of boric, boronic or borinic esters, and sometimes in the literature also as mono-, di- or trialkoxyboranes or borates.

The hydridosilane of the generic formula $Si_nH_m$ in the case that m=2n, is a cyclic hydridosilane and, in the case that m=2n+2, is a linear or branched hydridosilane. Processes for preparing hydridosilanes are known to those skilled in the art. The hydridosilanes present in the compositions according to the invention additionally have at least 5 Si atoms, i.e. n≥5.

Hydridosilanes consist of silicon and hydrogen atoms and have the advantage over carbon-containing organosilanes or hydrogen- and carbon-containing organosilanes that they react on conversion to give deposited silicon (optionally with a residual hydrogen content beneficial for the electronic properties) and gaseous hydrogen with no carbon content.

The content of hydridosilane, based on the overall formulation, may be 0.1% to 99% by weight, preferably 1% to 30% by weight.

Advantageously, the hydridosilane according to the invention is a hydridosilane oligomer preparable from at least one hydridosilane of the generic formula $Si_xH_{2x+2}$ with x≥3 or a cyclic hydridosilane of the generic formula $Si_xH_{2x}$ with x≥5, preference being given to hydridosilane oligomers preparable from linear or branched hydridosilanes. Hydridosilane oligomers are understood to mean hydridosilanes preparable from hydridosilanes with a comparatively lower molecular weight via an oligomerization. Hydridosilane oligomers are thus also hydridosilanes.

It is possible to use corresponding linear or branched hydridosilanes of the generic formula $Si_xH_{2x+2}$ with x≥3 in a particularly efficient manner, by a thermal route, to prepare hydridosilanes that are usable advantageously. More preferably, the hydridosilane is obtainable via thermal oligomerization of a composition comprising, as hydridosilane, essentially at least one hydridosilane of the formula $Si_xH_{2x+2}$ with x≥3-20 in the absence of a catalyst at temperatures of less than 235° C. Corresponding processes for preparing these compounds are disclosed in WO 2011/104147 A1. These compounds typically have weight-average molecular weights of 290 to 5000 g/mol (measured via GPC against a polystyrene standard). It is possible in a particularly efficient manner to prepare, by the process according to the invention, hydridosilane oligomers which are particularly suitable for use in the compositions according to the invention and have a weight-average molecular weight of 500-3500 g/mol.

Compositions of particularly good suitability are those which contain a hydridosilane of the generic formula $Si_nH_m$ which has been prepared by thermal means from a branched hydridosilane, most preferably from $Si(SiH_3)_4$ (neopentasilane).

Hydridosilanes of the generic formula $Si_nH_m$ that are usable advantageously may, however, also be preparable from a cyclic hydridosilane of the generic formula $Si_xH_{2x}$ with x=5 (cyclopentasilane).

The composition further comprises at least one compound of the formula $H_nB(OR)_{3-n}$ with R=$C_1$-$C_{10}$-alkyl, $C_6$-$C_{10}$-aryl, $C_7$-$C_{14}$-arylalkyl, halogen; n=0, 1, 2. Corresponding compounds are optionally alkylated, arylated, arylalkylated, halogenated and/or hydrogenated boric, boronic or borinic esters.

It was not known to date that boric, boronic or borinic esters can be used for doping, since it was assumed that the oxygen present therein has an adverse effect on the electrical properties of the resulting layers. DE 695 05 268 T2 does disclose processes for producing ceramic materials based on silicon carbide from polyalkylhydridosilanes and/or polyarylhydridosilanes in the presence of at least one boron compound, which may also include alkyl-substituted boric acid derivatives. However, the process described therein and the compositions disclosed for the purpose of production of ceramic materials are unsuitable for production of silicon-containing layers for the semiconductor industry. It has thus been found that, surprisingly, the stable boric, boronic or borinic esters are suitable as defined starting compounds for doping of silicon-containing layers and lead to good electrical conductivities of corresponding silicon-containing layers suitable for the semiconductor industry.

The content of boric, boronic or borinic esters, based on the overall formulation, is advantageously 0.0001% to 20% by weight, preferably 0.001% to 10% by weight and more preferably 0.01% to 5% by weight.

Most preferred compounds of the generic formula $H_nB(OR)_{3-n}$ are the compounds $H_nB(O(n-Bu))_{3-n}$ with n=1, 2. These compounds lead to very particularly good electrical properties of the silicon-containing layers preparable with the respective compositions.

Corresponding boric, boronic or borinic esters of the generic formula $H_nB(OR)_{3-n}$ with R=$C_1$-$C_{10}$-alkyl, $C_6$-$C_{10}$-aryl, $C_7$-$C_{14}$-aralkyl, halogen, n=0, 1, 2 can be purchased commercially or, for example, prepared in a controlled manner in situ from suitable precursor compounds.

Suitable precursor compounds for the in situ preparation of boric, boronic or borinic esters are $BH_3$, $B_2H_6$ in combination with aldehydes of the generic formula RHC=O, ketones of the generic formula RR'C=O, ethers of the generic formula R—O—R' with R, R'=$C_1$-$C_{10}$-alkyl, $C_6$-$C_{10}$-aryl, $C_7$-$C_{14}$-arylalkyl, or vicinal or 1,2 diols based on an alkyl or aromatic base skeleton, for example 2,3-dimethylbutane-2,3-diol, catechol; preferably with cyclic ethers of the generic formula $(CH_2)_nO$ (n=2-10) and most preferably with tetrahydrofuran $(CH_2)_4O$.

The composition according to the invention may consist exclusively of the hydridosilanes mentioned and the boric, boronic or borinic esters mentioned or have still further constituents.

It preferably contains further constituents for achievement of advantageous properties.

Thus, the composition preferably includes at least one solvent. Preferred solvents are aliphatic and aromatic hydrocarbons. Preference is further given to solvents from the group consisting of linear, branched and cyclic, saturated, unsaturated and aromatic hydrocarbons having one to 12 carbon atoms (optionally partly or fully halogenated), alcohols, ethers, carboxylic acids, esters, nitriles, amines, amides, sulphoxides and water. Particular preference is given to n-pentane, n-hexane, n-heptane, n-octane, n-decane, dodecane, cyclohexane, cyclooctane, cyclodecane, dicyclopentane, benzene, toluene, m-xylene, p-xylene, mesitylene, indane, indene, tetrahydronaphthalene, decahydronaphthalene, diethyl ether, dipropyl ether, ethylene glycol dimethyl ether, ethylene glycol diethyl ether, ethylene glycol methyl ethyl ether, diethylene glycol dimethyl ether, diethylene glycol diethyl ether, diethylene glycol methyl ethyl ether, tetrahydrofuran, p-dioxane, acetonitrile, dimethylformamide, dimethyl sulphoxide, dichloromethane and chloroform.

The proportion of solvent based on the overall formulation for achievement of advantageous properties may be 0.1% to 99.9% by weight, preferably 25% to 95% by weight.

Especially when the hydridosilane is obtainable via thermal oligomerization of a composition comprising, as hydridosilane, essentially at least one hydridosilane of the formula $Si_xH_{2x+2}$ with x≥3-20 in the absence of a catalyst at temperatures of less than 235° C., which has a weight-average molecular weight of 290-5000 g/mol, it is possible to achieve layers having particularly good properties when the formulation further includes a hydridosilane of the generic formula $Si_nH_{2n+2}$ with n=5-9.

The proportion of hydridosilane of the generic formula $Si_nH_{2n+2}$ with n=5-9 is, based on the mass of hydridosilane present, preferably 0.1% to 90% by weight, more preferably 1% to 30% by weight.

The inventive compositions are preferably coating compositions suitable for liquid phase processes. Most preferably, the compositions according to the invention are printing inks.

The present invention further provides a process for producing the compositions according to the invention, in which the at least one hydridosilane, the at least one compound of the generic formula $H_nB(OR)_{3-n}$ and any further constituents are mixed with one another.

The present invention likewise provides for the use of the composition according to the invention for production of silicon-containing layers. Preference is given to the use of the compositions according to the invention for production of doped silicon layers. Especially preferred is the use of the compositions according to the invention for production of p-doped, especially boron-doped, silicon layers.

Correspondingly, the present invention likewise provides a process for producing doped silicon-containing layers, preferably doped silicon layers, in which at least one composition according to the invention is applied to a substrate and converted thermally and/or with electromagnetic radiation to a doped silicon-containing layer, preferably a silicon layer.

The compositions according to the invention are advantageously suitable for the production of silicon-containing layers, preferably doped silicon layers, on a multitude of substrates. Silicon-containing layers are understood in the context of the present invention to mean not only essentially pure silicon layers but also layers which, as well as silicon, include further semiconductor metals, for example germanium; and additionally also layers containing silicon oxide, silicon carbide or silicon nitride.

Preferred substrates consist of glass, quartz glass, graphite, metal, silicon oxide, silicon, or a layer of silicon, silicon oxide, indium tin oxide, ZnO:F, ZnO:Al or $SnO_2$:F present on a heat-stable support. Preferred metals are aluminium, stainless steel, Cr steel, titanium, chromium or molybdenum. It is also possible to use polymer films, for example of PEEK, PEN, PET or polyimides, as substrates.

The compositions are preferably applied via a process selected from printing or coating processes, especially flexographic/gravure printing, nano- or microimprinting, inkjet printing, offset printing, digital offset printing and screen printing, spraying processes, aerosol assisted chemical vapour deposition, direct liquid injection chemical vapour deposition, spin-coating methods, dip-coating methods, and methods selected from meniscus coating, slit coating, slot-die coating and curtain coating.

After the application of the compositions and prior to the conversion, the coated substrate can still be dried in order to remove any solvent present. Corresponding measures and conditions for this purpose are known to those skilled in the art. In order to remove exclusively solvents, in the case of a thermal drying operation, the heating temperature should be less than 200° C.

In addition, preliminary crosslinking of the composition can be conducted on the substrate with UV irradiation.

The conversion is preferably effected at temperatures of 200-1000° C., preferably 250 to 750° C., especially preferably 300 to 700° C. In the thermal treatment of the coated substrate, the conversion is effected over a period of 0.1 ms-360 min. The conversion time is preferably between 0.1 ms and 10 min, especially preferably between 1 s and 120 s.

This comparatively rapid high-energy process regime can be effected, for example, by the use of an IR lamp, a hotplate, an oven, a flash lamp, a plasma with different gas composition, an RTP system or a microwave system, if required in the respective preheated or warmed state.

Conversion can likewise be effected by irradiation with UV light. The conversion time may preferably be between 1 s and 360 min.

After the conversion, enrichment of the silicon-containing layers with hydrogen can be conducted, called "hydrogen passivation" of defects in the silicon-containing layer as a result of unsatisfied "dangling" bonds, for example with reactive hydrogen by the hotwire method, with an oxygen-containing plasma, remotely or directly, under reduced pressure or under atmospheric pressure; or by means of corona treatment with supply of hydrogen, corona treatment being understood to mean a process for surface treatment of polymer films. Alternatively, the drying and/or conversion, as previously described above, can be conducted in a hydrogen-enriched atmosphere, such that the material is hydrogen-rich from the outset.

The coating operation described can be conducted more than once; simultaneous or subsequent deposition, in which case the films partly or completely overlie one another. In addition, the substrate may be coated on both sides.

The compositions according to the invention are suitable for a multitude of uses. They are of particularly good suitability—alone or in compositions with other constituents—for production of electronic or optoelectronic silicon-containing component layers.

The above-described use of the compositions according to the invention results in a distinct improvement in the technical feature of what is called the dark electrical conductivity, as disclosed by the description in Examples 1 and 2 which follow and the comparative example.

Dark electrical conductivity in the context of the present invention is a measure of the quality of the doping as a result of a lower defect density in the substrate described in each case.

What is noticeable is the dark electrical conductivity achieved according to Example 2, which is 5 orders of magnitude higher than that of the comparative example using the trialkylborane derivative $B(Et)_3$.

The significance of the boronic and borinic esters likewise present simultaneously alongside the boric esters in Example 2, which have been detected by NMR spectroscopy measurement, becomes apparent by comparison with Example 1.

In Example 1, doping is effected exclusively by the boric ester $B(O-n-Bu)_3$ and leads to a registered dark electrical conductivity ten times higher than that of the comparative example using the trialkylborane derivative $B(Et)_3$. Nevertheless, the coated substrate according to Example 2 has a dark conductivity 4 orders of magnitude higher compared to Example 1.

This technical effect was not foreseeable from the prior art.

The examples which follow are intended to provide further additional illustration of the use of the invention without having any limiting effect in themselves:
heteroemitter solar cells
HIT solar cells
selective emitter solar cells
back contact solar cells
field-effect transistors, thin-film transistors
dielectric layers in microelectronic components
surface passivation of semiconductor materials Abbreviations Used NPS=neopentasilane or tetrasilylsilane or $Si(SiH_3)_4$
NPO=neopentasilane-based silane oligomer
THF=tetrahydrofuran
RTP=rapid thermal processing
HIT=heterojunction with intrinsic thin layer

EXAMPLES

Example 1

To 1 g of NPO (Mw~2200 g/mol) was added 0.124 g of $B(O-n-Bu)_3$, and oligomerization was effected at 30° C. for 180 min. 0.1 g of the resulting p-doped NPO was formulated together with 0.069 g of cyclooctane and 0.161 g of toluene and the formulation was applied to a glass substrate. In a coating operation at 6000 rpm and a subsequent conversion operation at 500° C./60 s, it was possible to obtain a p-doped a-Si layer of 152 nm. The dark electrical conductivity is $2 \times 10^{-7}$ S/cm.

Example 2

Diborane (10% in $N_2$) was introduced into a mixture of 1 g of NPS and 0.035 g of THF, and oligomerization was effected at 30° C. over a period of 210 min. To 0.1 g of the resulting p-doped NPO were added 0.05 g of cyclooctane and 0.452 g of toluene. The resulting formulation was analysed by means of $^{11}$B NMR spectroscopy, and B(O-n-Bu)$_3$ ($\delta$ ($^{11}$B)=19 ppm (s)), HB(O-n-Bu)$_2$ ($\delta$($^{11}$B)=27 ppm (d, J$_{BH}$=160 Hz)), and H$_2$B(O-n-Bu) ($\delta$($^{11}$B)=8 ppm (t, $^1$J$_{BH}$=124 Hz)) were observed. In addition, the formulation was applied to a glass substrate. In a coating operation at 2000 rpm and a subsequent conversion operation at 500° C./60 s, it was possible to obtain a p-doped a-Si layer of 60 nm. The dark electrical conductivity is $1.1 \times 10^{-3}$ S/cm.

Comparative Example

To 5 g of NPS were added 2.587 g of B(Et)$_3$ (1 M in THF), and oligomerization was effected at 30° C. for 120 min. 0.1 g of the resulting p-doped NPO was formulated together with 0.05 g of cyclooctane and 0.45 g of toluene and the formulation was applied to a glass substrate. In a coating operation at 6000 rpm and a subsequent conversion operation at 500° C./60 s, it was possible to obtain a p-doped a-Si layer of 37 nm. The dark electrical conductivity is $2 \times 10^{-8}$ S/cm.

Experimental

All studies were conducted in gloveboxes produced by M. Braun lnertgas-Systeme GmbH or by means of standard Schlenk methodology (D. F. Shriver, M. A. Drezdzon, *The manipulation of air sensitive compounds,* 1986, Wiley VCH, New York, USA) under an inert atmosphere of dry nitrogen (N$_2$; O$_2$ content: <10 ppm; H$_2$O content: <10 ppm). Dry oxygen-free solvents (cyclooctane, toluene) were prepared by means of a solvent drying system of the MB-SPS-800-Auto type, manufactured by M. Braun lnertgas-Systeme GmbH. Deuterated benzene (C$_6$D$_6$) was sourced from Sigma-Aldrich, Coorp. and was stored over molecular sieve (4 Å) for at least 2 days prior to use for drying purposes. NMR spectra were measured on a spectrometer of the Varian INOVA 300 ($^{11}$B: 96.2 MHz) type from Varian, Inc., at room temperature. Chemical shifts are reported in comparison to an external reference (BF$_3$*Et$_2$O). The formulations described were made up at room temperature and applied to the substrate (EagleXG glass from Corning Inc.) by means of a PE syringe (including syringe filter: 1 µm). The wet films were produced with a Spincoat G3P-8 spin-coater from SCS Specialty Coating Systems, Inc. at 25° C. The conversion of the wet films was conducted on standard laboratory hotplates from HARRY GESTIGKEIT GmbH. Layer thicknesses were measured by means of a SENpro ellipsometer from SENTECH Gesellschaft für Sensortechnik mbH with defined angles of incidence between 40° and 90° (5° steps). Contact connection with the layers produced was achieved by the application of silver contacts by means of a sputtering system of the Emscope model SC 500 type from Quorum Technologies Ltd. Measurements for determination of dark electrical conductivity were conducted on a two-point measuring system from Keithley Instruments Inc. in an N$_2$ atmosphere and in the dark in a closed metal container at 25° C.

The invention claimed is:

1. A composition comprising:
   (i) at least one hydridosilane of formula Si$_n$H$_m$
      with n≥5 and
      m=(2n) to (2n+2), and
   (ii) at least one compound of formula H$_n$B(OR)$_{3-n}$
      with R=C$_1$-C$_{10}$-alkyl, C$_6$-C$_{10}$-aryl, C$_7$-C$_{14}$-arylalkyl, or halogen, and
      n=0, 1, or 2.

2. The composition according to claim 1, wherein the at least one hydridosilane is a hydridosilane oligomer prepared from a hydridosilane of formula Si$_x$H$_{2x+2}$ with x≥3 or a cyclic hydridosilane of formula Si$_x$H$_{2x}$ with x≥5.

3. The composition according to claim 2, wherein the hydridosilane oligomer is obtained via thermal oligomerization of a composition comprising, as hydridosilane, at least one hydridosilane of formula Si$_x$H$_{2x+2}$ with x≥3-20 in the absence of a catalyst at a temperature of less than 235° C.

4. The composition according to claim 3, wherein the hydridosilane of the formula Si$_x$H$_{2x+2}$ is neopentasilane.

5. The composition according to claim 2, wherein the hydridosilane of the formula Si$_x$H$_{2x}$ with x≥5 is cyclopentasilane.

6. The composition according to claim 1, wherein the compound of the formula H$_n$B(OR)$_{3-n}$ has a formula H$_n$B(OC$_4$H$_9$)$_{3-n}$ with n=1 or 2.

7. The composition according to claim 1, further comprising at least one solvent.

8. The composition according to claim 3, further comprising a hydridosilane of formula Si$_n$H$_{2n+2}$ with n=5-9.

9. A process for preparing the composition according to claim 1, comprising mixing the at least one hydridosilane, the at least one compound of the formula H$_n$B(OR)$_{3-n}$ and any further constituents.

* * * * *